(12) United States Patent  
Eastman et al.

(10) Patent No.: US 7,139,122 B1  
(45) Date of Patent: Nov. 21, 2006

(54) SYSTEM AND METHOD FOR ENHANCING CONFOCAL REFLECTANCE IMAGES OF TISSUE SPECIMENS

(75) Inventors: Jay M. Eastman, Pittsford, NY (US); Milind Rajadhyaksha, Charlestown, MA (US); James M. Zavislan, Pittsford, NY (US)

(73) Assignee: Lucid, Inc., Rochester, NY (US)

( * ) Notice: Subject to any disclaimer, the term of this patent is extended or adjusted under 35 U.S.C. 154(b) by 471 days.

(21) Appl. No.: 09/978,957

(22) Filed: Oct. 16, 2001

Related U.S. Application Data

(60) Provisional application No. 60/241,140, filed on Oct. 17, 2000.

(51) Int. Cl.  
*G02B 21/06* (2006.01)  
*A61K 49/00* (2006.01)

(52) U.S. Cl. .................. 359/386; 424/9.1

(58) Field of Classification Search ............ 359/368, 359/385, 386, 398; 600/476; 424/9.1, 9.8  
See application file for complete search history.

(56) References Cited

U.S. PATENT DOCUMENTS

| | | | |
|---|---|---|---|
| 4,298,590 A | 11/1981 | Bogoch | |
| 4,838,679 A | 6/1989 | Bille | |
| 4,863,226 A | 9/1989 | Houpt et al. | |
| 5,260,569 A | 11/1993 | Kimura | |
| 5,496,535 A | 3/1996 | Kirkland | |
| 5,733,739 A | 3/1998 | Zakim et al. | |
| 5,788,639 A | 8/1998 | Zavislan et al. | |
| 5,880,880 A | 3/1999 | Anderson et al. | |
| 5,995,867 A | 11/1999 | Zavislan et al. | |
| 6,134,009 A | 10/2000 | Zavislan | |
| 6,134,010 A | 10/2000 | Zavislan | |
| 6,187,289 B1 | 2/2001 | Richards-Kortum et al. | |
| 6,264,914 B1* | 7/2001 | Klaveness et al. ......... 424/1.65 |
| 6,319,488 B1* | 11/2001 | Licha et al. ................ 424/9.6 |
| 6,348,325 B1* | 2/2002 | Zahniser et al. .......... 435/40.5 |
| 6,498,945 B1 | 12/2002 | Alfheim et al. | |

FOREIGN PATENT DOCUMENTS

CN 1192930 A 9/1998

(Continued)

OTHER PUBLICATIONS

Burghardt, E., Colposcopy Cervical Pathology, Textbook and Atlas, Published by Thieme-Stratton, Inc., New York (1984), Foreward and pp. 112-120.

(Continued)

*Primary Examiner*—M. Robinson  
(74) *Attorney, Agent, or Firm*—Kenneth J. Lukacher

(57) ABSTRACT

A system using cross polarization effects and an enhancement agent having citric or other similar alpha hydroxy acid to enhance confocal microscope reflectance images and particularly images of the nuclei of BCCs (basal cell carcinomas) and SCCs (squamous cell carcinomas) in the confocal reflectance images of excised tumor slices obtained during Mohs surgery by illuminating the tissue being imaged (a tumor slice) using polarized light. The reflected illumination is passed to a polarization analyzer, which passes the polarization component which is crossed with respect to the polarization of the illuminating light. The light from the analyzer is passed through the confocal aperture and detected. The section of the tissue either at the surface or within the tissue is scanned and the reflectance image is produced with enhanced visualization of the cellular or nuclear structure thereof thereby enabling determination of the extent of the tumor (cancerous cells) in the section. A method is also provided using the system for diagnosing cancerous cells in skin tissue.

24 Claims, 2 Drawing Sheets

FOREIGN PATENT DOCUMENTS

WO        00/55669        9/2000

OTHER PUBLICATIONS

Fraschini, A. et al., The Effect of Different Fixatives on Chromatin: Cytochemical and Ultrastructural Approaches, Histochemical Journal, vol. 13, pp. 763-779 (1981).

Brochure, Looking Through The Window of Life, Lucid VivaScope, Lucid Technologies, Inc.

Amarante, Skin Care Products from Amarante featuring Alpha Hydroxy Acid, Printout of Web Site at http://www.amaranteskincare.com/, pp. 1-2, Jan. 24, 2002.

Rajadhyaksha et al., In Vivo Confocal Scanning Laser Microscopy of Human Skin: Melanin Provides Strong Contrast, The Journal of Investigative Dermatology, vol. 104, No. 6, Jun. 1995, pp. 946-952.

Rajadhyaksha and Zavislan, Confocal laser microscopy images tissue in vivo, Laser Focus World, Feb. 1997, pp. 119-127.

* cited by examiner

SYSTEM AND METHOD FOR ENHANCING CONFOCAL REFLECTANCE IMAGES OF TISSUE SPECIMENS

This application claims the benefit of priority to U.S. Provisional Patent Application No. 60/241,140, filed Oct. 17, 2000, which is herein incorporated by reference, and describes an improvement over International Application No. PCT/US00/07008, which was filed on Sep. 14, 2001 in the United States Patent and Trademark Office as U.S. patent application Ser. No. 09/936,535.

FIELD OF THE INVENTION

The present invention relates to confocal microscopy and particularly to a system (method and apparatus) for enhancing images of tissue at the surface or internally of a tissue sample so as to enable rapid and accurate screening of tissue for the determination of the nuclear and cellular structure thereof. The present invention also relates to a method for diagnosing cancerous cells in skin tissue using confocal microscopy. The invention is especially suitable in providing enhanced images of the nuclei of BCC/SCC (basal cell carcinoma or squamous cell carcinoma) in confocal reflectance images of tumor slices obtained during Mohs micrographic surgery. Tissue may be either naturally exposed, or surgically excised tissue.

BACKGROUND OF THE INVENTION

Mohs micrographic surgery for BCCs and SCCs involves precise excision of the cancer with minimal damage to the surrounding normal skin. Conventionally, precise excision is guided by histopathologic examination for cancer margins in the excised tissue slices during Mohs surgery. Typically, 2–4 slices are excised, and there is a waiting time of 10–30 minutes for the surgeon and patient while each slice is being processed.

Confocal reflectance microscopes can noninvasively image nuclear and cellular detail in living skin to provide images of tissue sections, such a microscope is described in U.S. Pat. No. 5,880,880. The contrast in the images is believed to be due to the detected variations in the singly back-scattered light caused by variations in refractive indices of tissue microstructure. Within the epidermal (basal and squamous) cells, the cytoplasm appears bright and the nuclei as dark ovals. The underlying dermis consists of collagen bundles and that, too, appears bright with dark spaces in-between. Thus, when neoplastic epidermal cells invade the dermis as in BCCs and SCCs, confocal detection of the cancers is very difficult because the cells and nuclei lack contrast relative to the surrounding normal dermis.

Acetic acid (vinegar) has been used as an image enhancement agent which enhances the back-scatter of light from certain cells. This is described, for example, in U.S. Pat. No. 5,733,739. When a tissue is illuminated with light of one polarization and a reflected image is detected via light of cross polarization the contrast of certain cells in the detected image is enhanced, when the tissue is treated by acetic acid, especially when the image is viewed via cross-polarized light in a confocal microscope. Such a system is described in the above referenced International Application No. PCT/US00/07008.

SUMMARY OF THE INVENTION

It is the feature of the present invention to provide an improved system and method for confocal microscopy by cross polarizing the light illuminating a tissue sample and the light returned from the tissue sample representing a section of the tissue and using an image enhancement agent other than acetic acid.

It is another feature of the present invention to use such cross polarizing of the light illuminating a tissue sample and the light returned from the tissue sample in combination with imaging the sample when immersed in an image enhancement agent containing citric acid or another alpha hydroxy acid.

It is a further feature of the present invention to provide a method for diagnosing cancerous cells in skin tissue using confocal microscopy and a citric or alpha hydroxy acid image enhancing agent to treat the tissue.

Briefly described, a system for providing enhanced images in confocal microscopy is provided by utilizing cross polarized light in the illumination of tissue and in the detection of light from which the images are formed, respectively, and where an image enhancing agent, which contains an effective amount of citric or similar alpha hydroxy acid, is used in a bath in which the tissue is immersed while being imaged. It will be understood that the agent may also be applied to tissue by coating, dipping or encapsulating in a gel of citric or other alpha hydroxy acid solution.

It has been found in accordance with the invention that a confocal laser scanning microscope using cross polarized components of light in illumination and in the detection of the reflected light from tissue specimens immersed in such an enhancement agent solution images of the cellular structure are enhanced, enabling cells and voids in the structure and the cell condition to be readily observed. By virtue of the use of such cross polarized light in imaging of tumor slices obtained in the course of Mohs surgery, epidermis sections which may have holes in the collagen are imaged more accurately so that holes are unlikely to be confused with cells or cell structure.

A method is also provided for detecting cancerous basal cell and squamous cell in dermal tissue with confocal reflected light imaging having the steps of: washing the tissue to be imaged with a solution of citric or other alpha hydroxy acid to whiten epithelial cells and believe to compact the chromatin of the tissue; imaging the tissue with a confocal microscope to provide confocal images of basal and squamous cells in which the confocal microscope directs light into the tissue and collects reflected light representing confocal images of the tissue; changing the polarization state of the light used by the confocal microscope to increase the contrast of the nuclei of basal and squamous cells in the confocal images; and analyzing the nuclei of the basal and squamous cells in the confocal images to diagnose which of such cells are cancerous.

BRIEF DESCRIPTION OF THE DRAWINGS

The foregoing features and advantages of the invention will become more apparent from a reading of the following description in connection with the accompanying drawings wherein.

DETAILED DESCRIPTION OF INVENTION

Figure 1:
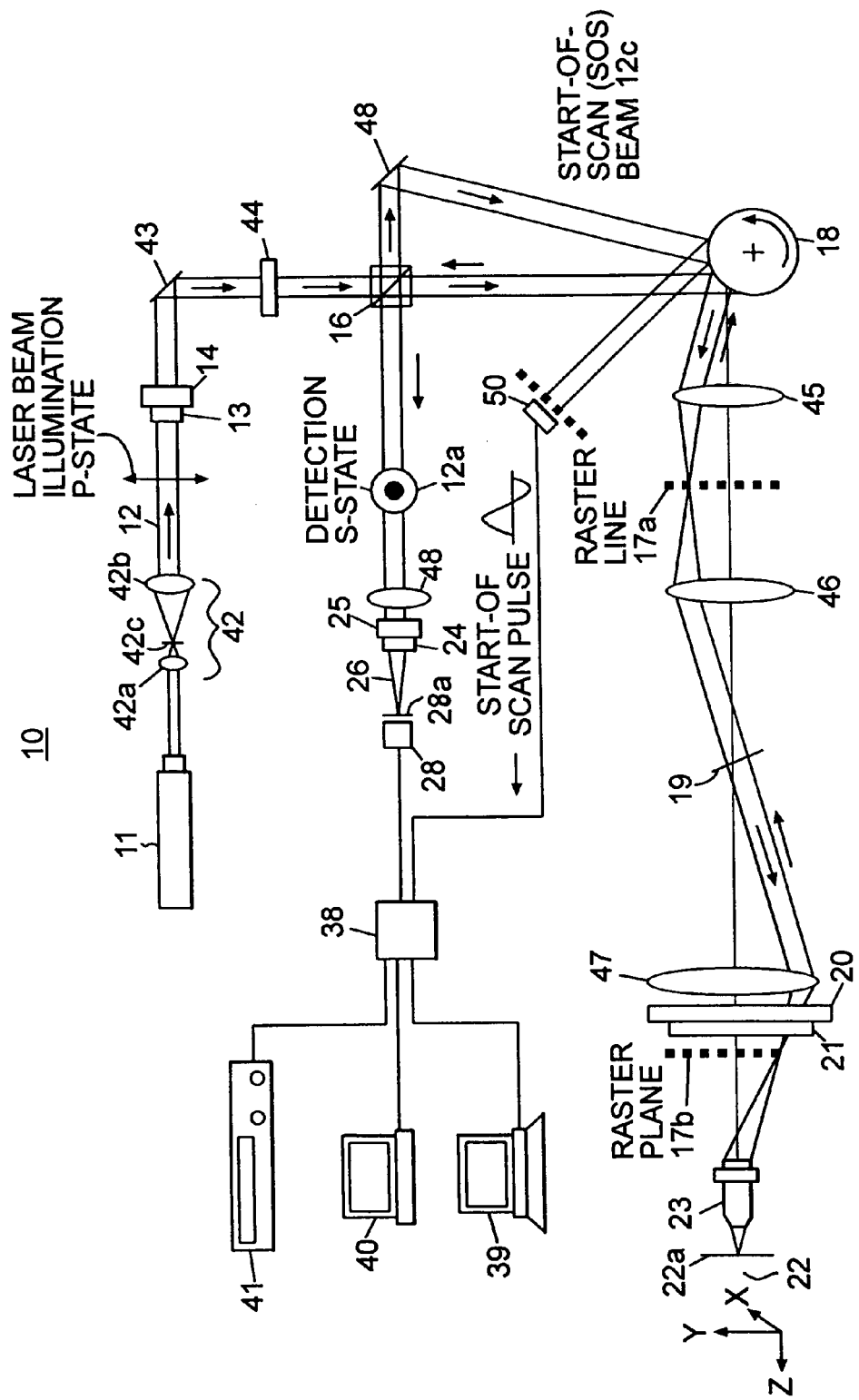
FIG. 1 is a schematic diagram of a Vivascope™ confocal microscope which is available from Lucid Inc. of Rochester, N.Y. and is described in the above referenced U.S. Pat. No. 5,880,880.
Figure 2A:
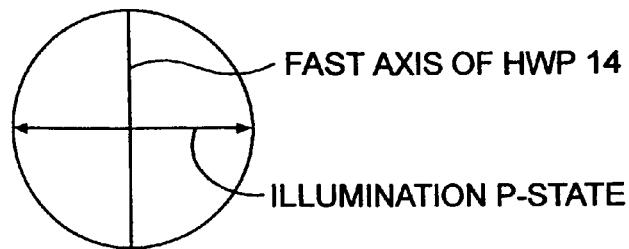
FIGS. 2A, B, C, and D are schematic depictions of various parts of the confocal microscope system and the cross-polarized illumination which is used therein.
Figure 2B:
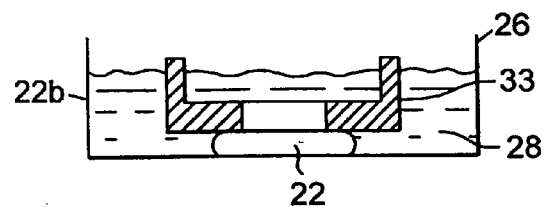
Figure 2C:
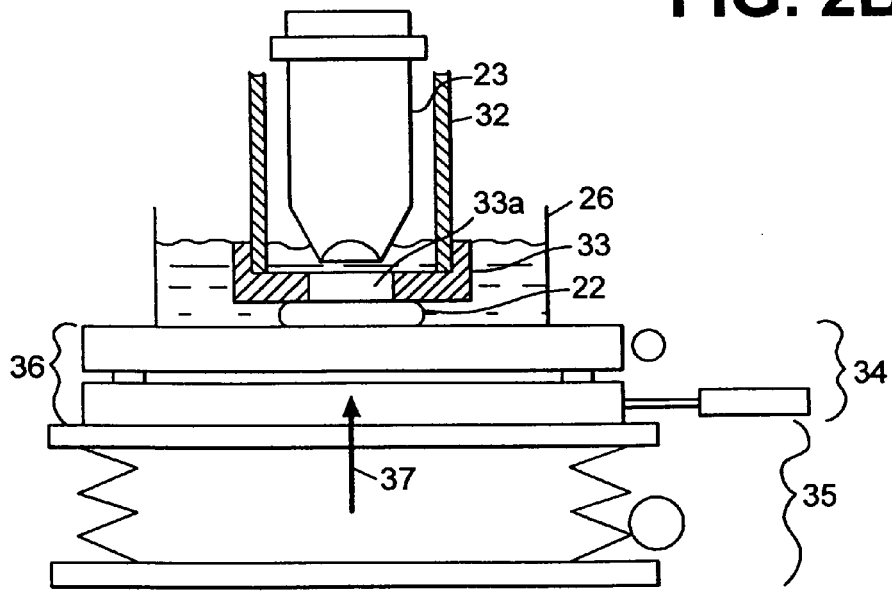

Referring to the drawings, in the confocal microscope 10 of FIG. 1, a linearly polarized (p-state) laser beam 12 is passed through a half wave plate (HWP) 13 on a rotation stage 14. A confocal microscope especially suitable in practicing the invention is described in U.S. Pat. No. 5,880,880, issued Mar. 9, 1999, which is herein incorporated by reference. Other confocal microscopes may also be used. The illumination through the non-polarizing or partially polarizing beam splitter 16 is scanned, as by a polygon mirror 18 and galvanometric mirror 19 across the specimen or sample 22 having a surface 22a. As shown in FIGS. 2B and 2C, sample 22 may be a BCC/SCC sample in a sample holder or container 22b contained in an enhancement solution bath 26 having water 28 under a tissue ring 33 which places the sample 22 under tension. As shown in FIG. 1, the microscope 10, via an objective lens 23, images the tissue sample 23 through an opening 33a in the tissue ring 33. For example, the opening 33a may include a window having a material transparent to the beam.

The target surface is the surface of the sample 22 (such as a tissue tumor specimen), which may be at the surface 22a or within the body of the sample, utilizing the techniques described in the above referenced U.S. Patent. The polarization of the incident light and the reflected light also can be modified using a quarter wavelength plate (QWP) 21 which is also removably mounted on a rotation stage 20.

Figure 2D:
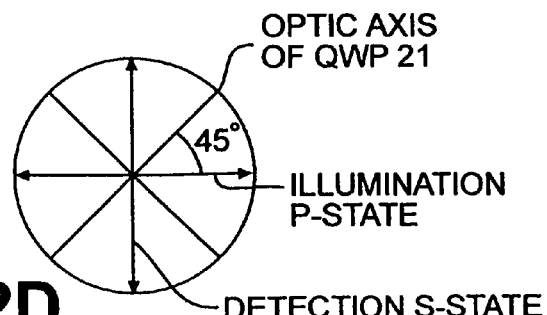

The detected light is cross-polarized that is in the s-state as shown by the bulls-eye indication 12a in FIG. 1 and labeled "detection s-state" in FIG. 2D. It is crossed or perpendicular or orthogonal to the p-state. Although preferably cross-polarized light is in s and p states, because the beam splitter may be non-polarizing or partially polarizing, other states are possible. The detected illumination of desired polarization is obtained with an analyzer 24 also mounted on a rotation stage 25. For example, analyzer 24 may be a linear polarizer. The light from the analyzer 24 is passed through the confocal aperture 28a, such as a pinhole, and a photo-detector 28, such as an avalanche photodiode (APD) in FIG. 1. While p polarized light from a linearly polarized laser 11 is shown in FIG. 1, the linearly polarized laser 11 and the half wave plate 13 can be replaced with a laser providing an unpolarized laser beam and a linear polarizer, respectively. Further, the linear polarizer and the analyzer 24 can then be replaced with a polarized beam splitter. Also, instead of rotating the half wave plate 13 and the analyzer 24, they can be kept fixed in cross polarization states and the sample 22 can be rotated.

As shown in FIG. 1, optical components are provided in confocal microscope 10 to direct the beam from laser 11 along a path to sample 22, and include, beam expander-spatial filter 42 (which, for example, may be provided by two lens 42a and 42b and aperture 42c), HWP 13, mirror 43, ND filter 44 (which, for example, may be a neutral density filter, such as provided by a circular variable attenuator manufactured by Newport Research Corporation), through beam splitter 16 to polygon mirror 18. The beam is then deflected by polygon mirror 18 through a lens 45 (which for example, may be a f/2 lens), a lens 46 (which for example, may be a f/5.3 lens), and deflected by galvanometric mirror 19 through a lens 47 (which for example, may be a f/3 lens), QWP 21 and objective lens 23 to sample 22. The optical components along the path of the reflected light returned from the sample 22 to detector 28 include, objective lens 23, QWP 21, lens 47, and deflected by mirrors 19 and 18 via lenses 46 and 45 to beam splitter 16. The beam splitter 16 directs the returned light through lens 48, analyzer 24, and pinhole 28a to detector 28. The raster line 17a and raster plane 17b in FIG. 1 are illustrated by dashed lines to denote the angular scan of the beam along a raster line 17a generated by the rotation of polygon mirror 18, while the angular movement of galvanometric mirror 19 scans that raster line to form a raster plane 17b. In this manner, a confocal image of a tissue section can be captured by the control electronics 38 through detector 28. To provide a start of scan beam 12c to synchronize the control electronics 38 with the start of each raster line, the beam splitter 16 directs part of the beam incident the beam splitter 16 to rotating polygon mirror 18, via mirror 48, to split diode 50 (e.g., photo-diode) which is connected to the control electronics 38 to provide a start of scan pulse at the beginning of each raster line. Motors, not shown, can provide the desired rotation and angular movement of respective mirrors 18 and 19.

The system which is shown in FIG. 1 operates as follows:

1. Remove QWP 21. Rotate the HWP 13 so that its fast axis is at 90 degrees with the illumination p-state (see FIG. 2A). Thus, there is no change (rotation) of the direction of the p-state. Rotate the analyzer 24 so that it acts as a crossed polarizer and transmits the detection s-state (which is orthogonal to the illumination p-state).

2. The surgically excised tissue sample 22 is placed in a water bath 26 with a tissue-ring 33 placed on top (see FIG. 2B).

3. The water bath 26 containing the sample 22 is placed under the objective lens 23, such that the tissue-ring 33 fits into the objective lens housing 31 (see FIG. 2C). The water bath 26 is on an XY translation stage 34 to move the sample 22. The XY stage 34 is on a lab-jack 35 with which can move the entire assembly 36 upwards, such that the sample 22 is gently pressed between the tissue-ring 33 and the water bath 26 to keep the sample 22 still during the imaging. Arrow 37 denotes the direction of such light pressure.

4. Rotate the HWP 13 in small angular increments of 10 degrees and, correspondingly, the analyzer 24 in angular increments of 20 degrees, on their respective stages 14 and 25, such that the analyzer 24 is always cross-polarized with respect to the illumination polarization state. The confocal images of the sample 22 change from bright to dark to bright as the HWP 13 and analyzer 24 is rotated.

5. Set the HWP 13 and analyzer 24 such that the sample 22 appears dark (i.e., minimum brightness). Survey the sample 22 by moving it with the XY stage 34, to check that the sample appears dark everywhere in the confocal images.

6. Lower the water bath 26 using the lab-jack 35. Remove the water from within the tissue ring 33, and add an enhancement agent, namely citric or other alpha hydroxy acid (e.g., to provide a 5% by volume—ph 2.5—solution in the water). Raise the lab-jack 35 and place the sample 22, as before, under the objective lens 23. It will be understood that the concentration of the solution to be effective may be in the range of from 3–20%.

7. Survey the sample 22 by moving it with the XY stage 34, and focusing on the surface and at varying depths of the sample with the objective lens 23 (which may be mounted on a Z-translation stage to move the objective lens towards and away from the sample). Confocal images are either videotaped or grabbed in this "crossed polarization" mode at a frame grabber 39, video monitor 40, or videotape recorder 41 via control electronics 38.

8. Whenever or wherever necessary, confocal images are obtained in "brightfield" mode, to either determine lateral or depth location, or identify structures (examples: hair follicles, sweat ducts, epithelial margins) within the sample. (This is analogous to using reflectance imaging in conjunction with fluorescence imaging.) The QWP 21 is inserted and rotated so that its optic axis is at 45 degrees to both the illumination and detection linear polarization states (see FIG. 2D).

With the confocal reflectance light microscope 10 described herein, BCCs, SCCs in human skin are described herein without the processing (fixing, sectioning, staining) that is required for conventional histopathology of Mohs surgery. Rapid confocal detection is provided after strongly enhancing the contrast of nuclei in the cancer cells relative to the surrounding normal tissue using citric or other alpha hydroxy acid and crossed polarization.

To improve the detection of BCCs and SCCs in confocal images in tissue, such as dermal tissue, which may be either naturally exposed, or surgically excised, the contrast of the nuclei of such cells is increased by the following method. The area of the tissue to be imaged is washed with 5% citric or alpha hydroxy acid, as described earlier. Citric or alpha hydroxy acid causes whitening of epithelial tissue and believe to cause the compaction of the chromatin. The chromatin-compaction is believed to increase its refractive index, which then increases light back-scatter from the nuclei and makes them appear bright. Next, the tissue area is imaged with confocal microscope 10 in which the polarization state of the light directed to the tissue and collected by the confocal microscope is controlled by rotating the linear polarizer of analyzer 24. When illuminated with linearly polarized light and confocally imaged through the analyzer 24, the brightness of the citric or alpha hydroxy acid-stained nuclei does not vary much, whereas the brightness of the collagen varies from maximum to minimum. The back-scattered light from the inter-nuclear structure is significantly depolarized (probably due to multiple scattering), whereas that from the dermis preserves the illumination polarization (due to single back-scatter). With the light in a crossed polarized state, bright nuclei in the BCCs and SCCs are shown in the confocal images produced by the microscope in strong contrast against a dark background of surrounding normal dermis. BCCs and SCCs can be distinguished from normal tissue by the cellular organization, cell size, cell shape, nuclear morphology, and cellular differentiation. One example of cellular organization is anaplasia. One example of cell size and shape and nuclear morphology is dysplasia. One example of cellular differentiation is pleomorphism.

Thus, the bright clusters of nuclei in the cancer cells are detectable at low resolution, as in conventional histopathology. Mosaics of low-resolution confocal images can be assembled to produce confocal maps of the BCCs or SCCs within the entire excised tissue. Detection of the cancers is made within minutes; thus, the total savings in time for a Mohs surgery can be hours.

Others cancers and tissue abnormalities may also be detected by using this approach any time a cellular tissue needs to be distinguished from acellular background. For example, dermal melanocytes, mucosal tissue in stromal tissue, breast epithelium in a stromal matrix.

From the foregoing description, it will be apparent that an improved system for enhancing images in confocal microscopy and method for diagnosing skin cancer cells is provided using citric or other alpha hydroxy acid. Variations and modifications in the herein described system and method will undoubtedly become apparent to those skilled in the art. Accordingly, the foregoing description should be taken as illustrative and not in a limiting sense.

The invention claimed is:

1. A system for providing enhanced images in confocal microscopy which is characterized by utilizing cross polarized light in the illumination of tissue and in the detection of light from which the images are formed, respectively, and wherein said tissue has an image enhancing agent containing an effective amount of an alpha hydroxy acid.

2. The system according to claim 1 wherein said alpha hydroxy acid represents citric acid.

3. The system according to claim 1 wherein said image enhancing agent is a solution of 3–20% concentration of said alpha hydroxy acid.

4. The system according to claim 1 wherein said image enhancing agent is a solution of 5% concentration of said alpha hydroxy acid.

5. The system according to claim 1 wherein said tissue is in a bath of said image enhancement agent.

6. The system according to claim 1 wherein said tissue is one of coated, washed, dipped, or rinsed with said image enhancing agent.

7. The system according to claim 1 wherein said image enhancing agent is one of a solution or gel.

8. The system according to claim 1 comprising:
   means for generating an illumination beam;
   optics for scanning the beam to the tissue and receiving returned illumination from the tissue representing a section of the tissue in which said optics has means for controlling the polarization state of the illumination beam and the returned illuminations to enable cross-polarization of the illumination beam with respect to the returned illumination; and
   means for detecting the returned illumination to form an image of the section of the tissue.

9. The system according to claim 8 wherein said polarization state controlling means comprises means for maintaining said cross-polarization of the illumination beam and the returned illumination from the tissue when the polarization state of the illumination beam and returned illumination are changed.

10. The system according to claim 9 wherein said light in the illumination beam is polarized in a p-state and the returned illumination is polarized to an s-state.

11. The system according to claim 8 wherein said image enhancing agent is capable of enhancing the brightness of one or more tissue structures in the image of the section of the tissue.

12. The system according to claim 8 wherein said tissue represent the excised tissue of a patient, said optics comprise at least an objective lens for focusing the illumination beam to the tissue and collecting returned illumination from the tissue, and said system further comprises:
   a container having a liquid of a solution with a concentration of said acid in which said tissue is disposed in said container in said liquid; and
   means for placing said tissue under tension against a surface in said container while enabling imaging of the tissue by said objective lens.

13. The system according to claim 8 further comprising means for moving said sample with respect to said objective lens.

14. The system according to claim 8 wherein said means for controlling the polarization state comprises means capable of changing the polarization of the illumination beam and the polarization of the returned illumination from the sample.

15. The system according to claim 14 wherein said means capable of changing the polarization comprises a half-wave plate and a quarter-wave plate through which passes said illumination beam to said sample, and a linear polarizer through which passes the returned illumination from said sample.

16. The system according to claim 15 wherein at least one of said half-wave plate, quarter-wave plate, and linear polarizer have means for rotation to change the polarization of the light passing there through.

17. The system according to claim 8 wherein said polarization controlling means is capable changing the polarization state of at least one of the illumination beam and the returned illumination to effect characteristics of tissue structures in the image of the tissue section to enable determination of which of the tissue structures are cancerous.

18. The system according to claim 8 wherein said tissue is skin tissue.

19. The system according to claim 8 wherein the tissue is one of naturally exposed tissue and surgically excised tissue.

20. The system according to claim 8 wherein said image enhancing agent is a solution of 3–20% concentration of said acid.

21. The system according to claim 8 wherein said image enhancing agent is a solution of 5% concentration of said acid.

22. The system according to claim 8 further comprising means for bathing said tissue in said image enhancing agent.

23. The system according to claim 8 wherein said image enhancing agent is one of a gel or solution.

24. The system according to claim 8 wherein said image enhancing agent is a gel which encapsulates said tissue.

* * * * *

UNITED STATES PATENT AND TRADEMARK OFFICE
CERTIFICATE OF CORRECTION

PATENT NO. : 7,139,122 B1  
APPLICATION NO. : 09/978957  
DATED : November 21, 2006  
INVENTOR(S) : Eastman et al.

It is certified that error appears in the above-identified patent and that said Letters Patent is hereby corrected as shown below:

On Title Page, item (73) Assignee, should read:
--(73) Assignees: Lucid, Inc., Rochester, NY (US); and
General Hospital Corporation, Boston, MA (US).--

Signed and Sealed this

Twenty-fifth Day of March, 2008

JON W. DUDAS  
*Director of the United States Patent and Trademark Office*